United States Patent [19]

Repperger et al.

[11] Patent Number: 4,842,607
[45] Date of Patent: Jun. 27, 1989

[54] ACCURATE HAND MOVEMENT ASSISTANCE

[75] Inventors: Daniel W. Repperger, Vandalia; Augustus Morris, Jr., Trotwood, both of Ohio

[73] Assignee: The United States of America as represented by the Secretary of the Air Force, Washington, D.C.

[21] Appl. No.: 58,466

[22] Filed: Jun. 5, 1987

[51] Int. Cl.[4] ............................................. A61F 2/72
[52] U.S. Cl. ..................... 623/24; 244/230; 244/234
[58] Field of Search ................ 623/24, 25, 66; 244/230, 830; 340/163

[56] References Cited

U.S. PATENT DOCUMENTS

| | | | |
|---|---|---|---|
| 3,523,665 | 8/1970 | Laynor, Jr. et al. | 244/83 |
| 3,733,039 | 5/1973 | O'Connor et al. | 244/77 R |
| 3,773,282 | 11/1973 | Sand et al. | 244/75 |
| 4,158,196 | 6/1979 | Crawford, Jr. | 340/163 |
| 4,302,138 | 11/1981 | Zaradiansky | 623/24 |
| 4,632,341 | 12/1986 | Repperger et al. | 244/230 |

Primary Examiner—Richard J. Apley
Assistant Examiner—David J. Isabella
Attorney, Agent, or Firm—Gerald B. Hollins; Donald J. Singer

[57] ABSTRACT

Hand movement assistance apparatus of both the active and passive types and usable for movement stabilization by either a normal human subject seeking to perform a task of great precision or a neurologically impaired human subject having Parkinson's disease or similar dysfunction. Both the active and passive apparatus provide a glove-like receptacle for the subject's hand; the passive system applies closed-loop feedback system generated forces to the glove and the active system provides a hand guidance track arrangement for the subject's hand. Three axis stabilization forces and rotationally oriented forces are alternatively provided by the active system, along with responses particularly adopted to the Parkinson's tremor frequency.

2 Claims, 1 Drawing Sheet

ACCURATE HAND MOVEMENT ASSISTANCE

RIGHTS OF THE GOVERNMENT

The invention described herein may be manufactured and used by or for the Government of the United States for all governmental purposes without the payment of any royalty.

BACKGROUND OF THE INVENTION

This invention relates to the filed of prosthesis apparatus for use in achieving precision movement and overcoming neurological dysfunction movements of a human limb.

Static and powered assistance devices to supplementn biological functions are now accepted practice in the medical and kindred arts. Externally-energized hearts for at least temporary use, artificial kidneys and electically-stimulated muscle usage have all become accepted practice in appropriate medical environments. In the present invention the extension of externally energized movement apparatus into the realm of neurological dysfunctions such as result from the effects of Parkinson's disease and into the realm of highly precise movements which may be beyond the capability of even normal human subjects is provided for. These extensions are in furtherance of the concepts recited generally in U.S. Pat No. 46,32,341 which issued to myself and several coinventors

SUMMARY OF THE INVENTION

The present invention provides for assisted movement of a human limb such as a hand and its appendages, and is usable in a variety of conditions wherein the unassisted movement provided by the human subject is unsatisfactory for accomplishing a predeterined task. Principal uses contemplated, therefore, for the invention include assistance to impaired function patients and extension of the normal range of human ovements into the realm of greater precision and smaller dimensional capabilities. Such capabilities are provided in the present invention by an externally energized, preferably electrical, apparatus which opposes and steadies the tendency of normal and impaired muscular movement of the tremor type with precision forces having direction and amplitude that are guaged to overcome performance limiting tremor. Assistance is also provided by way of a guidance arrangement in the invention.

According to the preferred arrangement of the invention, the assisted test subject is connected to an assistance apparatus by means of an appliance such as a glove, which fits over the hand of the test subject and is driven by externally-energized transducers that provide forces to oppose the hand tremor. The tremor opposing forces are gauged as to direction and magnitude in response to sensors such as accelerometers which are also disposed on the user's glove. A feedback path between the sensor and the gove forcing transducer elements is provided and this feedback path may include amplifiers and signal processing apparatus which may be of the hardwired or electronic computer variety.

An object of the present invention is, therefore, to provide a closed-loop human limb movement assistance apparatus.

Another object of the invention is to provide a movement assistance apparatus which may be used for either enhancing precision movement capabilities in a test subject or for enhancing impaired function movements in a test subject.

Another object of the invention is to provide a limb movement guidance apparatus which may be used during the performance of specified tasks by test subjects.

Another object of the invention is to provide a movement assistance arrangement in which the assistance force transmitting elements allow a degree of user-initiated movement flexibility.

Another object of the invention is to provide a movement assistance apparatus in which conplementary motion by opposing energy transducer elements provides a desirable range of user functional reach and other advantages.

Another object of the invention is to provide a user motion assistance arrangement which may be arranged to oppose rotational tremor movements or alternately, may be active along a plurality of coordinate axes.

Additional objects and features of the invention will be understood from the followig description and the accompanying drawings.

These and other objects are achieved by stabilization apparatus for attenuating living subject hand tremor movements comprising the combination of a force coupling member receivable on a hand portion of the subject, motion-sensing transducer means connected with the coupling member for generating an electrical signal responsive to acceleration movement of the hand portion, electrical-to-mechanical transducer means mechanically coupled with the force coupling member for applying electrically generated physical force thereto, and signal processing means electrically coupled with the motion-sensing transducer means and the electrical-to-mechanical transducer means for converting the motion-sensing transducer acceleration signal to a larger electrical-to-mechanical transducer means energizing signal and for energizing the electrical-to-mechanical transducer means into tremor movement opposing mechanical motions.

DETAILED DESCRIPTION

Figure 1:
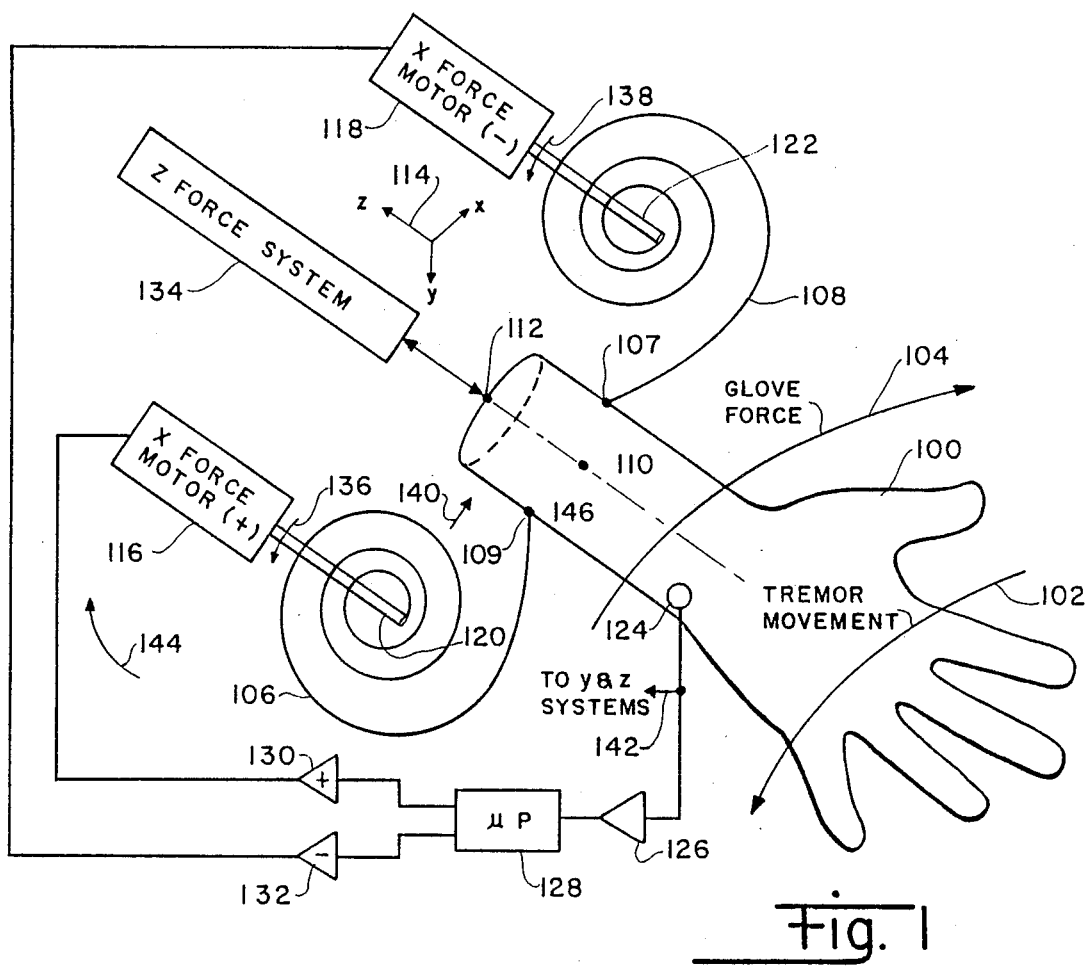
FIG. 1 is an oblique view of a hand movement stabilization apparatus made in accordance with the invention.

FIG. 1 in the drawings shows an accurate hand movement stabilization apparatus made in accordance with the invention. The FIG. 1 apparatus includes a glove member 100 in which is received the hand of the human subject whose movement is to be stabilized. The human user's hand which is received in the glove 100 is presumed to be subject to tremor movement as represented by the arrow 102 in FIG. 1. Such movement may be the result of either normal physiological response to conditions such as agonisticantagonistic muscle transfer—response exceeding the degree of tremor acceptable for the task to be performed or alternately, may be of a grosser or more severe nature as might result from neurological dysfunction. Such dysfunction may be of the type resulting from Parkinson's disease and other neurological disorders. In response to the tremor movement 102, the FIG. 1 stabilization apparatus provides a stabilizing and assisting counterforce which is indicated by the arrow 104 in FIG. 1.

Generation of the stabilizing and assisting force 104 in FIG. 1 involves the closed-loop feedback system which is generally indicated by the arrow 144. Included in this feedback system is an acceleration sensor 124 mounted on the glove 100, the acceleration signal amplifier 126, a signal processing apparatus such as the microprocessor 128, power amplifiers of opposite polarity 130 and 132, and the positive and negative force generating motors or transducers 116 and 118. The force motors 116 and 118 each include an output shaft 120 and 122 which is connected by coupling arrangements such as the torsion springs 106 and 108 to suitable attachment points 1077 and 109 located at convenient forcing locations on the glove 100. Gearing or crank and lever or other mechanisms may be included between the motors 116 and 118 and the attachment points 107 and 109 in order to achieve desirable coupling between the motor and glove in other embodiments of a FIG. 1 system.

The FIG. 1 apparatus also includes glove attachment points for Y-axis and Z-xis force generating systems which are shown at 110 and 112, respectively; such systems may also be desired in other embodiments of the invention. A Z-axis force generating system is indicated in block form at 134 in FIG. 1. Also shown in FIG. 1 is an identification of the coordinate axes and their directions 114, and a coupling path 142 by which signals from the accelerometer 124 may be applied to Y- and Z-axis force generating systems where such systems are employed; a three-axis responsive version of the accelerometer 124 is, of course, contemplated when a Y- and Z-axis active system is used. The arrow 140 in FIG. 1 indicates the principal direction of movement, that is, movement along the X axis which is contemplated for the illustrated motors 116 and 118.

Operation of the FIG. 1 hand movement stabilization system contemplates the sensing of a tremor or other undesired movement signal by the accellerometer 124 and use of the output information from thi accelerometer to generate signals suitable for driving the motors 116 and 118 to oppose or counteract the sensed tremor signal. The generation of motor energizing signals from the accelerometer signal may involve several signal processing operations, including amplification of the accelerometer signal to suitable convenient amplitude levels in the amplifier 126 and enhancement of the processed output signals to eh amplitude, current level, time characteristics and other signal attributes required for opeation nof the motors 116 and 118. The amplification portion of this processing is indicated at 130 and 132 in FIG. 1. Depending upon the type of otors used at 116 and 118, the energization signal may assume a variety of different electrical forms, including inter alia a pair of phase displaced alternating current signals where each of the motors 116 and 118 is of the induction type. Signals supplied to the motors 116 and 118 may also be of an amplitude and polarity varying direct current nature where brush-type motors having a wound armature and either a permanent magnet or electromagnetic field coil are used. Alternately, the motor energizing signals may be of the pulsed variety when stepping motor, rotoary solenoid, or other discrete movement machines are employed for the motors 116 and 118.

The indicated positive and negative polarities of othe power amplifiers 130 and 132 relate principally to the direct current motor case, and more precisely to an embodiment wherein identical motors are used in conjunction with identical couplings e.g. identical springs at 106 and 108. The oppositely wound spring members 106 and 108 shown in FIG. 1 circumvent the need for opposite polarities from the power amplifiers 130 and 132 in the strictest sense of the FIG. 1 drawing. Generally it may be stated that some provision for complementary movement of the attachment points 1077 and 109 is desirable in the FIG. 1 apparatus, and this complementary movement may be provided either by the illustrated oppositely-wound springs or by oppositely polarized motors or amplifier outputs oro by other means known in the electrical and mechanical arts. In view of the illustrated opposite winding directions of the springs 106 and 108 in FIG. 1, the rotational directions of the motors 116 and 118 are shown to be coincident, as indicated at 136 and 138 in FIG. 1.

Use of the torsion spring members 106 and 108 allows some flexibility in positioning of the glove 100 by the FIG. 1 assisted human subject while also transmitting the desired movement opposing forces. Other coupling arrangements, including other forms of spring members, or alternatively limited torque motors which may be overpowered by the assisted subject, may be used as the motors 116 and 118. The springs 106 and 108 are shown to be of the tensile or tension nature, that is, capable of exerting tension or pulling forces with little capability for exerting comprssion or pushing forces, and are thereby used in complementary pairs where each spring may serve principally in a tension role. Double-acting springs capable of both tension and compression usage may, of course, be substituted in FIG. 1 with the elimination of one motor and spring and one of the attachment points 1077 and 109. In the illustrated single attachment points for the Y and Z axis forces at 110 and 112, such double-acting tension and compression springs are implied.

The stabilization apparatus shown in FIG. 1 of the drawings contemplates use of orthogonally directed or X, Y and Z axis forces for opposing tremor movement 102. The contemplated X, Y and Z forces are, of course, capable of opposing any direction of movement of the human subject's hand by suitable combinations or additions of force components in the X, Y and Z directions. An alternate to this three orthogonal axis approach may also be employed where the movement to be stabilized is limited to a rotational tremor of the type shown by the arrow 102. Rotational tremor in a Parkinson's disease paptient frequently has a natural frequency in the rangne of 4 Hz. Rotational forces can be accomplished by the motors 116 and 118 in FIG. 1 by suitable relative positionings of the motors, springs, and attachment points to the glove 100—so that forces are applied to diametrically opposite sides of the glove with respect to a centroidal axis 146 and rotation abou the centroidal axis 146 results. For the rotational tremor movement, stabilization may be achieved with a single pair of motors and sprgs or with one double-acting motor and spring combination.

Signal processing for the FIG. 1 apparatus is located between the amplifiers 126 and 130–132 and accomplished several functions. This processing may be performed by a conventional microprocessor illustrated at 128 in FIG. 1. Functions performed in the signal processing include the followig:

(1) Electrical wave filtering tending to emphasize the signal frequency band surrounding a frequency of 4 Hz—the principal frequency of tremor when the FIG. 1 apparatus is used with a Parkinson's patient.

(2) Analog-to-digital conversion of the signals received from the accelerometer 124. This conversion may be achieved in a hardwired A-to-D converter or performed by software such as a subroutine.

(3) Generation of the motor energizing signals dictated by the accelerometer 124, signals that are format disposed according to the motors employed at 116 and 118, i.e., phase displaced waveforms, amplitude and polarity varying DC, or pulses as recited above.

(4) Elecltive adjustment of amplitude and frequency response of the FIG. 1 apparatus by the operator to suit the varying tasks of a given user subject of the FIG. 1 apparatus and also variations between different user subjects of the FIG. 1 apparatus.

Several variations of the FIG. 1 illustrated apparatus are within contemplation of the invention. The glove 100 for example, may be made from a variety of materials, however, a heavy rubber construction with suitable reinforcementn at the points of attachment 107, 109, 110 and 112 are preferred. It is desirable for the glove to provide relatively rigid connection to the user subjects's hand while also permitting movement of the user's fingers and accomplishment of normal movement tasks. The gearbox recited earlier herein and located between the motors 116 and 118 and the points of attachmentn 1077 and 109 to the glove 100 is especially desirable for use with high-speed motors, motors of small physical size, but high rotation rates—in order to match the motor rotation rate with the relatively slow movements of a human subject. Slow speed motors or hydraulic couplings or other arrangements in lieu of the gearbox and arrangement shown in FIG. 1 may, of course, be provided by persons skilled in the mechanical art.

Figure 2:
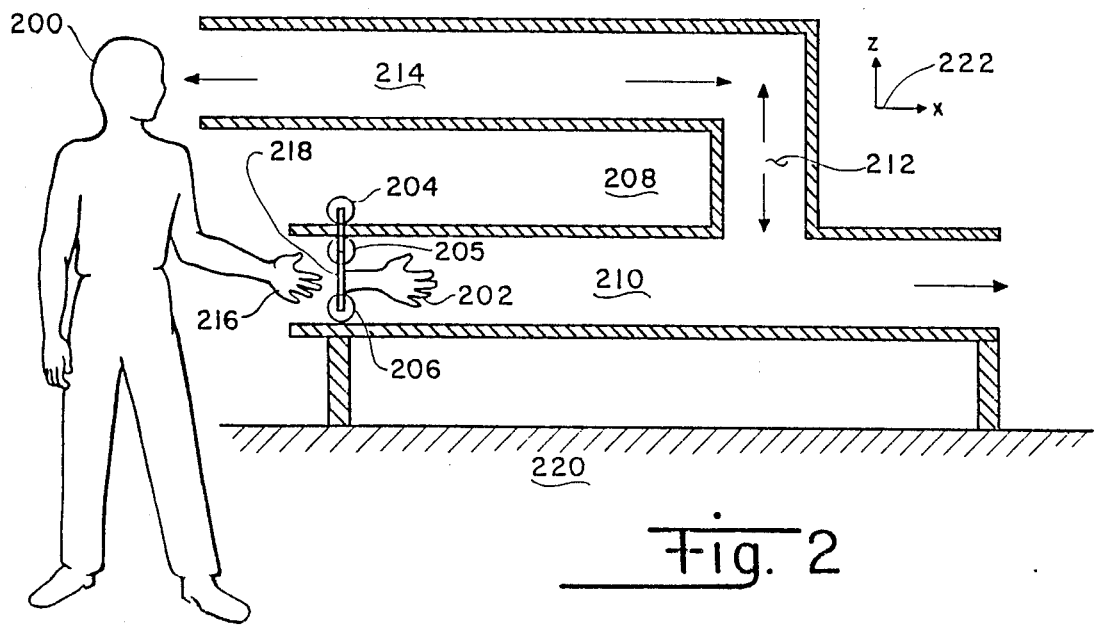
FIG. 2 is a schematic diagram of a hand guidance apparatus according to a further aspect of the invention.

Turning now to FIG. 2 in the drawings, there is shown in FIG. 2 an exemplary two-degree of freedom rail track arrangement which may be additionally used for hand movementn stabilizlation by a human subject for specific purposes such as eating or the performance of repeated tasks. The X and Z direction freedoms present in the FIG. 2 apparatus are indicated at 222 in FIG. 1. Rail track arrangements such as illustrated in FIG. 2 may be used for example, to provide eating assistance for a human subject. Eating has been found to be one of the more difficult but obviously necessary tasks for a patient with advancing neurological dysfunction. Eating assistance being the principal intended use of the FIG. 2 illustrated rail track apparatus.

In the FIG. 2 apparatus, a human subject 200 using the rail track apparatus 208, would insert a hand 216 into he glove 202 in order that hand movementn be limited to the X direction tracks 210 and 214, and the Z direction track 212. Movement along the tracks 210, 212, and 214 is provided by a roller trolley apparatus 218 which includes the roller members 204 and 206 which engage the tracks 210, 212 and 214 in a positive and movement-limiting manner. Movement along the tracks is therefore enabled while tremor movements are restrained.

The physical arrangment of the tracks 210, 212 and 214 in FIG. 2 are particularly adapted to acts of eating wherein a movement along the track 214 enables transfer of eating utensils to the user's mouth while movement along the track 212 enables elevation from the level of food engagement to the level of the user's mouth, and movement along the track 210 enables the user to engage food items on the table 220. The rail track apparatus 208 may therefore be resident upon a table surface 220. Rollers in addition to the group shown at 204 and 206 in FIG. 2 are of course, contemplated for engagement with the vertically oriented portions of the track apparatus 208; in a more complete embodiment of the FIG. 2 apparatus in fact, the trolley 218 would have some multipel faceted shape and a plurality of rollers or other friction members disposed one ach facet in order that convenient movement between the tracks 210, 212 and 214 be feasible. Shown at 212 is a three- or four-roller arrangement of the trolley apparatus 218. Rail track apparatus configured in other patterns and disposed on the floor, a wall, or other mountings may, of course, be used within the spirit of the invention.

While the apparatus and method herein described constitute a preferred embodimentn of the invention, it is to be understood that the invention is not limited to this precise form of apparatus or method, and that changes may be made therein without departing from the scope of the invention, which is defiined in the appended claims.

We claim:

1. Stabilization apparatus for attenuating living subject hand tremor movements comprising the combination of:

a force coupling member receivable on a hand portion of said subject;

motion-sensing transducer means connected with said coupling member for generating an electrical signal responsive to acceleration movement of said hand portion;

electrical-to-mechanical transducer meansn mechanically coupled with said force coupling member for applying electrically generated physical force thereto;

signal processing means electrically coupled with said motion-sensing transducer means and said electrical-to-mechanical transducer means for converting said motion-sensing transducer acceleration signal to a larger electrical-to-mechanical transducer means energizing signal and for energizing said electrical-to-mechanical transducer means into tremor movement opposing mechanical motions; and a frequency responsive filter element having selective response to signals of four Hertz frequency disposed in a predetermined location along a signal ltransmission path joining said motion-sensing transducer means, said signal processing means, and said electrical to mechanical transducer means.

2. Stabilization apparatus for attenuating human subject limiting tremor movements comprising the combination of:

a stabilization force coupling member receivable on a hand portion of said subject;

first motion-sensing transducer means conected with said force coupling member for generating an electrical signal responsive to components of said hand portion tremor movements parallel to a first axis in an orthogonal axis set surrounding said hand portion;

second motion-sensing transducer means connected with said force coupling member for generating an electrical signal responsive to components of said hand portion tremor movements oriented parallel to the second axis of said orthogonal axis set;

first electrical-to-mechanical transducer means mechanically coupled with said force coupling member for applying first electrically-generated physical forces, parallel with said first axis, to said force coupling member and said hand portion;

second electrical-to-mechanical transducer means mechanically coupled with said force coupling member for applying second electrically-generated physical forces, parallel with said second axis, to said force coupling member and said hand portion;

first signal processing means electrically coupled with said first motion-sensing transducer means andn said first electrical-to-mechanical transducer means for converting said motion-sensing transducer acceleration signal to a larger first electrical-to-mechanical transducer means energizing signal and for energizing said first electrical-to-mechanical transducer means into first tremor movement opposing mechanical motion parallel with said first axis; and second signal processing means electrically coupled with said second motion-sensing transducer means for converting said second motion-sensing transducer acceleration signal to a larger second electrical-to-mechanical transducer means energizing signal and for energizing said second electrical-to-mechanical transducer means into second tremor movement opposing mechanical motion parallel with said second axis.

* * * * *

UNITED STATES PATENT AND TRADEMARK OFFICE
CERTIFICATE OF CORRECTION

PATENT NO. : 4,842,607

DATED : June 27, 1989

INVENTOR(S) : Daniel W. Repperger et al

It is certified that error appears in the above-identified patent and that said Letters Patent is hereby corrected as shown below:

```
Col 1. line 11, correct the spelling of "field".
Col 1, line 15, correct the spelling of "supplement".
Col 1, line 28, change "46,32,341" to --4,632,341--.
Col 1, line 36, correct the spelling of "predetermined".
Col 1, line 39, change "ovements" to --movements--.
Col 2, line 11, correct the spelling of "complementary".
Col 2, line 20, correct the spelling of "following".
Col 3, line 13, change "1077" to --107--.
Col 3, line 37, correct the spelling of "accelerometer".
Col 3, line 38, change "thi" to --this--.
Col 3, line 46, change "eh" to --the--.
Col 3, line 48, change "opeation nof" to --operation of--.
Col 3, line 50, change "otors" to --motors--.
Col 3, line 61, correct the spelling of "rotary".
Col 3, line 64, change "of othe" to --of the--.
Col 4, line  6, change "1077" to --107--.
Col 4, line  9, correct the spelling of "oppositely".
Col 4, line 10, change "oro" to --or--.
Col 4, line 26, correct the spelling of "compression".
Col 4, line 32. change "1077" to --107--.
Col 4, line 48, correct the spelling of "patient".
Col 4, line 49, correct the spelling of "range".
Col 4, line 54, correct the spelling of "about".
Col 4, line 57, correct the spelling of "springs".
Col 4, line 60-61, change "accomplished" to
        --accomplishes--.
Col 4, line 64, correct the spelling of "following".
Col 5, line 10, correct the spelling of "Elective".
Col 5, line 19, correct the spelling of "reinforcement".
Col 5, line 25, correct the spelling of "attachment".
Col 5, line 26, change "1077" to --107--.
```

UNITED STATES PATENT AND TRADEMARK OFFICE
CERTIFICATE OF CORRECTION

PATENT NO. : 4,842,607

DATED : June 27, 1989

INVENTOR(S) : Daniel W. Repperger et al

It is certified that error appears in the above-identified patent and that said Letters Patent is hereby corrected as shown below:

```
Col 5, line 37, correct the spelling of "movement
       stabilization".
Col 5, line 41, change "1" to "2".
Col 5, line 50, correct the spelling of "the".
Col 5, line 50, correct the spelling of "movement".
Col 6, line  5, correct the spelling of "multiple".
Col 6, line  7, change "one ach" to --on each--.
Col 6, line 15, correct the spelling of "embodiment".
Col 6, line 19, correct the spelling of "defined".
Col 6, claim 1, line 10, correct the spelling of "means".
Col 6, claim 1, line 26, correct the spelling of
       "transmission".
Col 6, claim 2, line 6, correct the spelling of "connected".
Col 7, claim 2, line 29, correct the spelling of "and".
```

Signed and Sealed this

Seventeenth Day of July, 1990

*Attest:*

HARRY F. MANBECK, JR.

*Attesting Officer*  *Commissioner of Patents and Trademarks*